United States Patent [19]

Norlien et al.

[11] Patent Number: 5,042,500
[45] Date of Patent: Aug. 27, 1991

[54] DRYING SAMPLE LINE

[75] Inventors: John A. Norlien, St. Paul; Kurt J. Michler, Vadnais Heights, both of Minn.; A. Gerrit Crawford, San Francisco, Calif.

[73] Assignee: Medical Graphics Corporation, St. Paul, Minn.

[21] Appl. No.: 539,130

[22] Filed: Jun. 18, 1990

[51] Int. Cl.$^5$ ............................................. A61B 5/097
[52] U.S. Cl. ................................. 128/719; 128/205.27
[58] Field of Search ........... 128/716, 719, 911, 205.12, 128/205.27

[56] References Cited

U.S. PATENT DOCUMENTS

| | | | |
|---|---|---|---|
| 4,463,764 | 8/1984 | Anderson et al. | |
| 4,637,384 | 1/1987 | Schroeder | 128/911 |
| 4,676,239 | 6/1987 | Humphrey | 128/911 |
| 4,958,075 | 9/1990 | Mace | 128/719 |

OTHER PUBLICATIONS

Nova-Ventir catalog for Co-Ax Ventilator Circuit.

*Primary Examiner*—William E. Kamm
*Assistant Examiner*—Robert L. Nasser, Jr.
*Attorney, Agent, or Firm*—Haugen and Nikolai

[57] ABSTRACT

A drying sample line for coupling a patient's expiratory gases to a gas analyzer consists of first and second concentrically disposed tubes where the innermost tube is fabricated from Nafion plastic. The expiratory gas is drawn through the lumen of the Nafion inner tube and, simultaneously, dried air is made to pass through the lumen of the outer tube in a counterflow direction relative to the expiratory gases. Because of the properties of the Nafion plastic, water vapor (moisture) contained in the expiratory gas being coupled to the analyzer passes through the wall of the Nafion tube and into the dried air stream. In this fashion, the water vapor is removed from the expiratory gas mixture being applied to the analyzer.

2 Claims, 1 Drawing Sheet

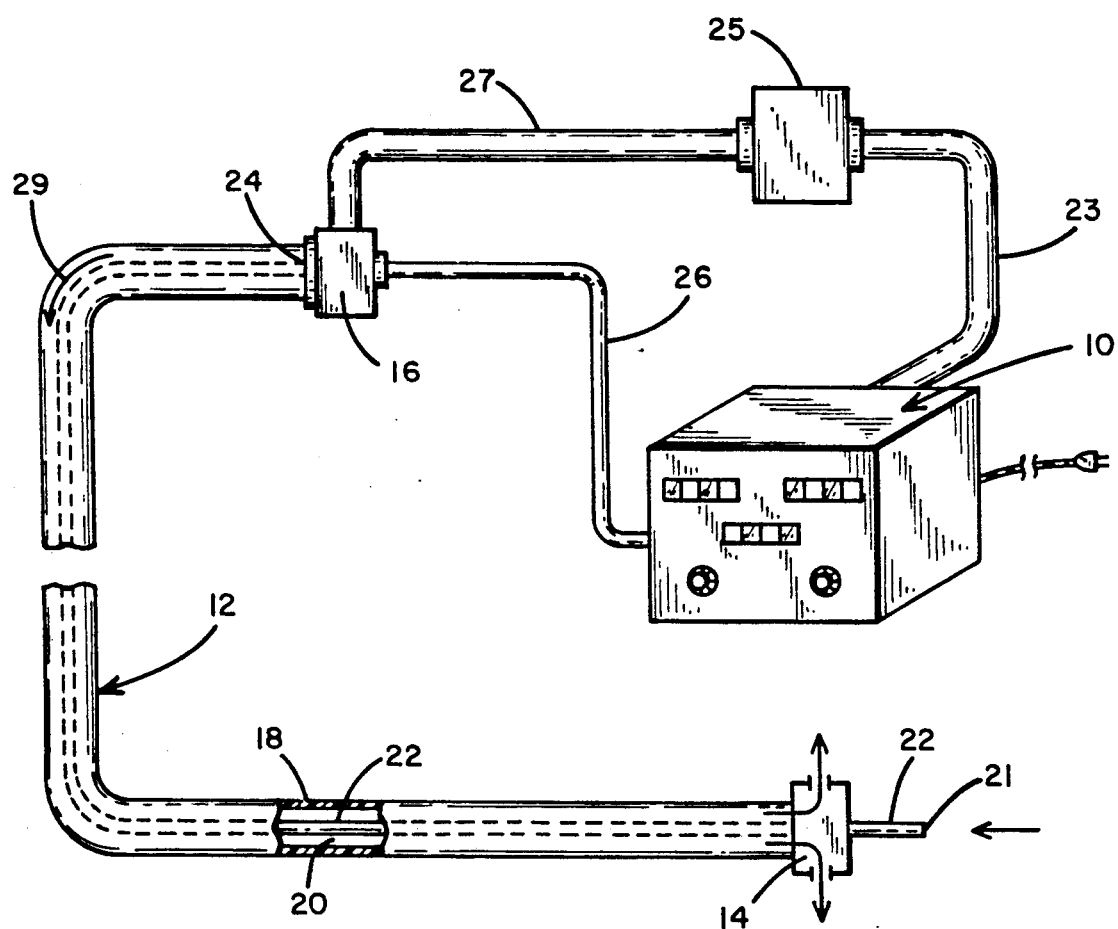

DRYING SAMPLE LINE

BACKGROUND OF THE INVENTION

I. Field of the Invention

This invention relates generally to cardiopulmonary test equipment, and more particularly to apparatus for conveying a respiratory gas mixture breathed by a patient to the gas analyzer apparatus in which water vapor is effectively extracted from the mixture during its flow from the patient's mouthpiece, mask or head.

II. Discussion of the Prior Art

In equipment of the type disclosed in the Anderson, et al. U.S. Pat. No. 4,463,764 and assigned to applicant's assignee, various parameters to be measured include the partial pressure of $CO_2$ and $O_2$ contained in a breath sample. Where measurements are to be performed on a breath-by-breath basis, it is essential that the volume of the sample tube used to convey the expiratory gas mixture to the analyzer be kept as small as possible to provide a short transport time and to minimize distortion of the waveform. Moreover, it is desired that the gas sample be dry, i.e., free of water vapor by the time it reaches the analyzer. While in-line desiccators may be effective to remove moisture from a gas stream flowing therethrough, such devices, to be effective, must be of a size wherein the volume involved no longer accommodates breath-by-breath analysis.

OBJECTS

It is accordingly a principal object to the present invention to provide a drying sample line for coupling a patient's mouthpiece, mask or hood to a respiratory gas analyzer.

Another object of the invention is to provide a drying sample line whose volume does not interfere with a breath-by-breath response time.

Yet another object of the invention is to provide a drying sample tube for coupling a patient's mouthpiece or hood to a respiratory gas analyzer which is simple in construction and sufficiently low in cost that it can be considered a disposable.

SUMMARY OF THE INVENTION

The foregoing features, objects and advantages of the invention are achieved by providing a drying sample tube comprising an elongated flexible plastic outer tube having an inlet end, an outlet end and a lumen extending between those two ends. Coaxially fitted within the lumen of the outer tube is an inner tube having a predetermined small internal diameter consistent with breath-by-breath response times, the inner tube being fabricated from a perfluorinated polymer sold by the DuPont Corporation under the trademark Nafion ®. The Nafion plastic employed exhibits high permeability to moisture (water vapor) but does not readily pass other respiratory gases, such as oxygen and carbon dioxide. The inlet end of the inner tube is joined to the patient's mouthpiece, facemask or hood and its outlet end is coupled through the gas analyzer devices to a source of negative pressure, such as provided by a vacuum pump. The output of the vacuum pump is then coupled through a desiccator to the lumen of the outer tube of the drying sample line at a point proximate the outlet end of the inner tube. The dry air desiccated is thus made to pass in the counterflow direction relative to the gas stream sample passing through the inner tube and the moisture passing through the wall of the Nafion tube mixes with the dried air.

DESCRIPTION OF THE DRAWING

The constructional features and mode of operation of the preferred embodiment will become more apparent to those skilled in the art from the following detailed description of the preferred embodiment when considered in conjunction with the accompanying drawing illustrating the invention.

DESCRIPTION OF THE PREFERRED EMBODIMENT

Referring to the drawing, there is indicated generally by numeral 10 a respiratory gas analyzer capable of measuring and indicating the concentration or partial pressure of constituent gases contained within a breath sample. In that the invention principally relates to the sample drying tube employed to carry the respiratory gas from the patient to the analyzer module 10, it is deemed unnecessary to describe in detail the features of that module, suffice it to say that it includes a vacuum pump which is operative to develop a negative pressure at its inlet and a positive pressure at its outlet.

The drying sample tube is identified generally by numeral 12 and is seen to include a patient interface adapter 14 at the respiratory gas inlet end thereof and a coupler 16 at its outlet end for allowing the drying sample tube 12 to be operatively coupled between the patient and the respiratory gas analyzer module 10.

The drying sample tube itself comprises an outer tubular jacket 18 which may be made of polyvinyl chloride, silicon rubber, polyurethane, polyethylene or other material commonly used as medical tubing. The outer tube or jacket 18 has a lumen 20 extending the full length thereof from the adapter 14 to the adapter 16. Contained within the lumen 20 is an inner tube 22 having an internal diameter of relatively small dimension so that, given the overall length of the tube, the total volume occupied by the lumen of the inner tube 22 remains sufficiently small to meet the transport time requirements of the system.

In accordance with the present invention, the inner tube 22 is fabricated from Nafion, a perfluorinated ion exchange polymer exhibiting high permeability to the transfer of water vapor therethrough, but low permeability to other respiratory gases which may travel down the lumen of the tube 22. The Nafion material transfer the water vapor under the influence of a driving force related to the concentration difference across its walls.

A relatively short coupling tube 26 is shown as being used to join the outlet end 24 of the inner tube 22 to the gas analyzer 10. The actual devices used to measure partial pressure or percent concentration of constituent gases in the respiratory gas stream are coupled in line with the tube 26 and to the inlet of the vacuum pump (not shown). When the pump is operating, then, exhaled gases entering the inlet end 21 of the inner tube 22 are drawn through the lumen of that tube and through the analyzing devices contained within module 10. The pump's outlet is coupled through a tube 23 to the inlet side of an air dryer or desiccator 25 and the outlet side of that device is, in turn, coupled by a tube 27 and the adapter module 16 to the lumen of the outer tube or jacket 18. Thus, dry air is made to flow through the jacket in the direction of arrow 29. This direction is counter to the direction of the respiratory gas flow in the lumen of the inner tube 22.

Because of the moisture permeability properties of the Nafion tube 22, water vapor contained within the respiratory gas sample passes through the wall of the tube 22 and into the dried air stream flowing through the lumen 20 of the outer jacket 18. As such, the gas sample reaching the analyzer module 10 is effectively void of moisture. The external tube 18 also serves to protect the Nafion tube from skin oils, mechanical tearing or puncture.

Accurate measurement of the concentration of a particular gas in an expired mixture, requires that the relative humidity of the room air must be accurately known or appropriate steps must be taken to eliminate water vapor as a variable in the computation. In the case of the present invention, the drying sample line ensures that the breath sample reaching the $O_2$ and $CO_2$ analyzers contains no water vapor.

The dimensions of the sample drying line in terms of the internal diameter and length of the Nafion tube and the size of the lumen of the outer jacket are established in the first instance to meet the flow rates and pressure drops acceptable when performing breath-by-breath analysis. This, too, depends upon whether the patient in question is an adult, a child or a neonate. The apparatus must also present a sufficiently high resistance to flow such that transient surges in the operation of the vacuum pump do not alter the readings obtained from the $O_2$ and $CO_2$ analyzers employed. In fact, in some applications, it may be desirable to match the sample line to the analyzer in terms of its flow resistance characteristics.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed:

1. A device for removing water vapor from a respiratory gas stream comprising:
   (a) a first elongated flexible tube having an inlet end and an outlet end and a lumen extending between said inlet and outlet ends;
   (b) a second elongated flexible tube made from a perfluorinated ion exchange polymer material exhibiting a relatively high permeability to the transfer of water vapor compared to other respiratory gases, said second tube having an inlet and an outlet end and a lumen extending between said inlet and outlet ends, said second tube being disposed within said lumen of said first tube;
   (c) means for drawing moisture laden respiratory gases into said inlet end of said second tube; and
   (d) means for flowing dry air through said lumen of said first tube from said inlet end to said outlet end of said first tube in a direction opposite to the direction of flow of said respiratory gases in said second tube.

2. The device as in claim 1 wherein said inlet end of said second tube extends outwardly beyond said outlet end of said first tube and said outlet end of said second tube extends outwardly beyond said inlet end of said first tube.

* * * * *